United States Patent [19]
Wortrich

[11] Patent Number: 5,282,787
[45] Date of Patent: Feb. 1, 1994

[54] FLUID TRANSFER SYSTEM INCORPORATING DISPOSABLE CASSETTE

[75] Inventor: Theodore S. Wortrich, Long Beach, Calif.

[73] Assignee: Surgin Surgical Instrumentation, Inc., Tustin, Calif.

[21] Appl. No.: 975,870

[22] Filed: Nov. 13, 1992

Related U.S. Application Data

[63] Continuation-in-part of Ser. No. 596,219, Oct. 12, 1990, Pat. No. 5,163,900, which is a continuation-in-part of Ser. No. 324,018, Mar. 16, 1989, Pat. No. 4,963,131.

[51] Int. Cl.$^5$ .............................................. A61M 1/00
[52] U.S. Cl. ............................................ 604/30; 604/34
[58] Field of Search ..................... 604/30, 34, 35, 200

[56] References Cited

U.S. PATENT DOCUMENTS

| | | |
|---|---|---|
| Re. 33,250 | 7/1990 | Cook . |
| 3,308,810 | 10/1967 | Galin . |
| 4,187,057 | 2/1980 | Xanthopoulos . |
| 4,425,116 | 1/1984 | Bilstad et al. ................ 604/34 |
| 4,475,904 | 10/1984 | Wang . |
| 4,493,695 | 1/1985 | Cook . |
| 4,537,561 | 8/1985 | Xanthopoulos . |
| 4,627,833 | 12/1986 | Cook . |
| 4,728,228 | 7/1988 | Williams ........................ 604/34 |
| 4,904,168 | 2/1990 | Cavoto et al. . |
| 4,963,131 | 10/1990 | Wortrich ........................ 604/34 |
| 5,125,891 | 6/1992 | Hossain et al. ................. 604/34 |
| 5,163,900 | 11/1992 | Wortrich ........................ 604/34 |
| 5,195,960 | 3/1993 | Hossain et al. ................. 604/34 |

Primary Examiner—Paul J. Hirsch
Attorney, Agent, or Firm—Raymond A. Bogucki

[57] ABSTRACT

A system for controlling the irrigation and aspiration functions in flow lines cooperative with a surgical control console employs separate interacting cooperative units for the segregation of different functions in units employed in different ways. A receiver unit is configured to fit within a cassette receptacle in a console but does not perform any function apart from transferring forces with internal slider bars. The receiver accepts a slidable adapter which in turn receives a small disposable cassette that provides some internal irrigation and aspiration lines, and an external aspiration line that is separately threadable through the adapter unit to cooperate with a peristaltic pump in the console.

25 Claims, 3 Drawing Sheets

FLUID TRANSFER SYSTEM INCORPORATING DISPOSABLE CASSETTE

CROSS-REFERENCE TO RELATED APPLICATION

This application is a continuation-in-part of pending application Ser. No. 07/596,219, filed Oct. 12, 1990, now U.S. Pat. No. 5,163,900 entitled DISPOSABLE CASSETTE SYSTEMS, which is a continuation-in-part of U.S. Pat. No. 4,963,131 entitled DISPOSABLE CASSETTE FOR OPHTHALMIC SURGERY APPLICATIONS, issued May 4, 1990, both of which are assigned to the assignee of the present invention, and both of which are incorporated by reference herein.

BACKGROUND OF THE INVENTION

Disposable cassette systems are widely used, particularly in medical applications involving the handling of fluids that interact with biological systems. Examples are to be found in U.S. Pat. Nos. 4,493,695, 4,627,833, and 4,713,051.

Where blood is the fluid being transferred, the dangers of contamination are high, and consequently it is generally preferred to utilize disposable tubing and fluid transfer systems rather than attempt to sterilize part or all of the fluid handling system for each use. Incorporation of the essential elements in a relatively low cost cassette minimizes removal and handling time and the dangers of an incorrect setup. The same is true in fluid interchange systems used for ophthalmic surgical applications, such as irrigation and aspiration systems of the type sold by Site Microsurgical Systems, Inc., a Johnson & Johnson subsidiary, under their Model No. TXR, and by CooperVision, Inc., now Alcon, under the Model 10,000. The Alcon Model 10,000 is essentially described in U.S. Pat. No. 4,713,051 to Steppe, et al., and represents a cassette adaptation of an earlier Model 8000 that employed loose tubing sets with peristaltic pumps and passed waste matter to a plastic bag. The Site cassette, as evidenced by U.S. Pat. No. 4,627,833 to Cook, disposes flexible irrigation and aspiration tubings in a rectangular housing having an attached rigid collection vessel through which a reciprocating pump draws a vacuum. In both systems internal flexible lines are juxtaposed so that after the cassette is inserted, line flow can be stopped by clamp actuators in the console which pinch exposed portions of flexible lines against internal surfaces. In operation of both systems, sterile irrigation fluid from a source is fed by gravity to the operative site, and aspirated fluid is pumped from the operative site back to a collection unit.

The Alcon cassette is configured in a known fashion so as to provide a semicircular boss against which the rollers of the peristaltic pump press the irrigation line to force aspiration fluid along.

In the parent U.S. Pat. No. 4,963,131, entitled DISPOSABLE CASSETTE FOR OPHTHALMIC SURGERY APPLICATIONS, issued May 4, 1990, it is shown that the use of internal sliders within a cassette body to transfer force from an external clamp actuator internally into a selected location or locations within the cassette has a number of particular advantages. By confining the area of repeated flexure of the transfer lines to well within the body of the cassette, the danger of contamination of sterile flows from the occurrence of cracks or pinholes in the line due to repeated flexure is greatly minimized. Also, the line geometries within the cassette are straightened, shortened and simplified by virtue of the degrees of design freedom that are available.

In the other parent application to the instant application, Ser. No. 07/596,219, now U.S. Pat. No. 5,163,900 it is shown that the use of separate, interacting cooperative units and the segregation of the supply or irrigation function from the aspiration, pumping and control functions provides substantial advantages. A receiver structure is inserted in the cassette receiving surface or receptacle of the system and provides a flow path for the pumping and transfer of aspiration fluid from the operative site to a collection receptacle. The geometry is also arranged such that the receiver defines an open sided interior volume within which a smaller second disposable unit can be inserted. The smaller disposable unit includes fittings for lines connecting a sterile fluid source to the operative site. The combination of receiver and cassette includes those fittings and internal tubing needed for connection of the aspiration lines to a vent or other form of vacuum control on the system console. Internal sliders in the receiver act upon lines in the disposable cassette to simplify and shorten the internal tubing geometry and provide contamination safeguards. Thus a disposable conduit system is provided that connects the aspiration flow path from the handpiece to the waste collection unit, while sterile fluid pathways are incorporated in a smaller disposable cassette. Prior to the introduction of this concept, cassettes for surgical tubing systems were based on the premise that all operative tubing and other parts must be located within a housing so that by virtue of this prepackaging of the entire unit only external connections need be made.

The cost of disposable cassettes is, however, an item of constant concern as health care expenses continue to mount. Further decreases in the cost of disposable units, without sacrifice of sterility or operative advantages are much to be desired. Improvements in the ease of and safety of handling and installation are also to be incorporated wherever possible. Fundamental reorganization of functions and relationships in an interconnect and control system that extends the features disclosed in the parent application shows how these results can be obtained.

SUMMARY OF THE INVENTION

Substantial advantages are achieved in accordance with the invention by apparatus and methods which use separate, interacting cooperative units and a small disposable cassette to effect the necessary functions with means which are distributed throughout the different units, some of which are used many times while the cassette is used only once. By integrating configuration with function, manual steps can be carried out in instinctive fashion with substantial cost saving but no material risk of error.

In an example of cassette devices and systems in accordance with the present invention, a receiver structure is configured to be insertable within the cassette receiving surface or receptacle of the control system and thereafter retained in place during the sequential use of many disposables. An open sided interior volume that is defined in the receiver receives a conforming smaller second and multiple use adapter unit. The adapter unit is slidably insertable in the receiver structure and itself includes a small cassette-receiving receptacle open at its superior surface. A small disposable cassette unit containing sterile irrigation tubing and interior backup surfaces for clamping the tubing is then inserted into the second unit and discarded after each operative procedure. The cassette includes an exterior length of tubing that is readily threaded through a preconfigured path in the adapter for engagement with an aspiration pump.

In a specific example of such a cassette system, the receiver unit includes slider elements and the adapter unit includes an adjacent open-topped tubing pathway extending adjacent a backup surface for a peristaltic pump. The receiver includes a front access tray on which the adapter is supported while the cassette is loaded in place, after which the adapter and cassette are slid into position and held by a spring loaded retainer. The cassette is shaped with a inserted end that has a protruding central region and adjacent apertures, and has internal lengths of tubing that are clamped through the apertures by the sliders on the receiver. The aspiration tubing in the cassette includes means in the protruding central region of the cassette for engaging a vacuum control conduit on the console. An external length of output tubing extending from the side of the cassette is insertable in the tubing pathway of the adapter unit when the cassette is in place. The nested combination of receiver, second unit and disposable cassette includes those interconnections used in control of flow in aspiration lines by the system console, while the slider configuration simplifies and shortens the internal tubing geometry and provides contamination safeguards in the sterile area. Incorporation of the sliders in the receiver further reduces the cost of the small disposable cassette without affecting the sterile passageways. The adapter unit not only receives the cassette and provides a peristaltic pump backup surface, but the simple threading step involved in connecting the aspiration tubing to the output is carried out with a minimum of time and inconvenience. Because the adapter and cassette can be shifted in and out of position relative to receiver at the front access tray on the receiver, the exchange of cassettes is straightforward and rapid, since the threading of the aspiration line is self-deforming. The arrangement eliminates hardware otherwise included in the disposable, reduces the tubing used, and provides fail-safe loading.

With this arrangement also, all the needed internal functions and connections are provided but the segregation of parts and functions within separate units of different degrees of permanence substantially reduces the total cost of using cassettes in performing a number of operative procedures.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
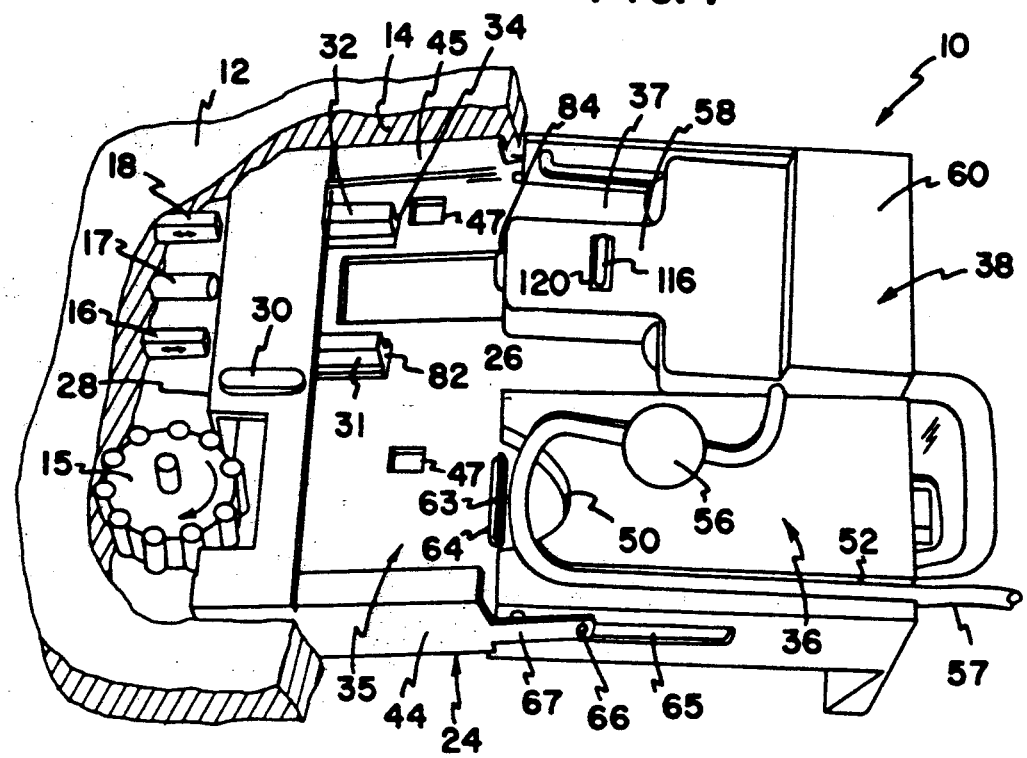
FIG. 1 is a perspective view of a system in accordance with the invention utilizing a receiver, adapter unit and disposable cassette combination, the adapter unit and cassette being in a loading position before insertion in the receiver, which is in the cassette receptacle of a control console.
Figure 2:
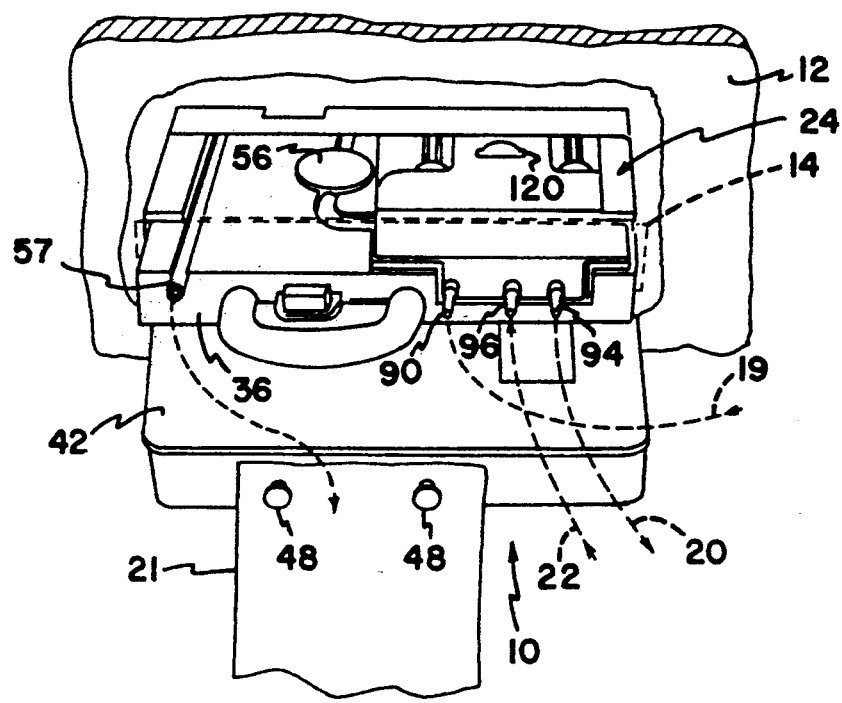
FIG. 2 is a perspective view of a system in accordance with the invention in operative position in a console.

A modular tubing and interconnect system 10 in accordance with the invention is shown in FIGS. 1 and 2, as adapted for use with the console 12 of a widely used commercial type of irrigation/aspiration system for ophthalmic surgery, specifically the CooperVision (now Alcon) Model 10,000. The console 12 is shown only in fragmentary form, and only certain functions of this console 12 that are relevant to the movement and control of flow of fluids to and from a surgeon's handpiece are shown, in generalized manner. The console 12 includes a cassette receptacle 14 (FIG. 2) of generally rectangular outline, having a front opening leading to an inner edge along which are a number of serially disposed operative elements. These operative elements (seen in FIG. 1 only) comprise a peristaltic roller pump 15, a shunt line actuator 16, a vacuum control system (VCS) line 17 and an irrigation line actuator 18 (seen only in FIG. 1). The VCS line 17 couples to operator-accessible controls, by which a surgeon or assistant can control suction on the aspiration line and also control pump rate.

Although other orientations may be used, the receptacle 14 in practice (See FIG. 2) has its principal length in the horizontal direction. The horizontal direction, as well as the anterior (front face) and posterior (internal face) regions of the receptacle 14 will be referred to for convenience, it being understood that this is by way of example only and that other orientations are feasible.

When in this orientation, the peristaltic roller pump 15 rotates about a vertical axis, and its periphery describes an arc within the receptacle 14, to provide the characteristic roller pumping action on a adjacent flexible line. The shunt line actuator 16 and the irrigation line actuator 18 comprise bar elements moving in the posterior-anterior direction when actuated. The bar elements pinch or close off flexible lines disposed in their path, or engage slider mechanisms for effecting clamping action as disclosed in U.S. Pat. No. 4,963,131, issued Oct. 16, 1990 to Surgin Surgical Instrumentation, Inc. reference herein. The surgeon has a foot control (not shown) by which he can stop the pump or reduce the vacuum.

Sterile irrigation fluid from a supply bottle flows under gravity through a flexible line 19 (FIG. 2) which can be closed by the irrigation line actuator 18 before it passes to the conventional handpiece at the surgical site via a length of irrigation tubing 20, indicated schematically in FIG. 2. Fluid, tissue and debris are extracted from the surgical site via the handpiece, under the differential pressure (suction) created by the peristaltic roller pump 15 as it acts on the adjacent flexible line. The pump 15 draws the withdrawn aspiration fluid along an aspiration line 22 from the handpiece up to a cassette and then passes it out to a waste container 21. The suction level at the VCS line 17 is varied at the console 12 by the system, the surgeon, or other operating staff. In this system a flexible shunt line between the irrigation and aspiration flow is, as described below in greater detail, normally closed off by the shunt line actuator 16. The shunt line may however be opened to permit backflow of irrigation fluid toward the handpiece so as to clean out adhering debris and provide rapid vacuum relief.

In accordance with this specific example of the present invention, three separate units having separate functions and durations of use are engaged within the cassette-receiving receptacle 14 in partially nesting relation (FIGS. 1 and 2). A permanent but removable receiver 24, (FIGS. 1 and 3 particularly), which is approximately rectangular in top view has a body portion 26 that fits within the console receptacle 14 (FIGS. 1 and 2). The receiver 24 has a leading or inserted edge 28 that extends into the posterior portion of the receptacle 14. When the second and third units are nested in the receiver 24, as described below, various internal elements are operatively positioned relative to the roller pump 15, actuators 16 and 18 and VCS fitting 17, respectively. A guide bar 30 on the leading edge of the top of the receiver ensures proper alignment of the receiver 24 with the receiver receptacle 14 of the console 12 during insertion. A pair of sliders 31, 32 are mounted on bars 33, 34 (FIG. 3 only) in the posterior region of the receiver 24, to be in alignment with and reciprocated by the separate actuators 16, 18. The receiver 24 has an outer margin that defines an open-topped volume 35, best seen in FIG. 1, in which a cassette adapter unit 36 (FIG. 4) may be placed. The adapter receiving volume 35 is of generally rectangular form and configured to accept, guide and retain. The multiple use cassette adapter unit 36 has a shaped concavity 37 (FIG. 4) on one side for holding a small disposable cassette 38. The concavity 37 is on the right side of the adapter unit 36 (as seen in the entry direction) so that the cassette 38 is aligned with the operative elements 16-18 in the console 12 and the sliders 31, 32 in the receiver 24. The left-hand side of the adapter unit 36 is in opposition to the peristaltic pump 15.

The adapter unit 36 is supportable in either of two positions on the receiver 24, because the anterior lower edge of the receiver 24 is shaped as a service apron 42 (FIGS. 2 and 3) that descends downwardly from the receiver body portion 26. The adapter unit 36 may thus be seated adjacent the console at an angle on the service apron 42 so that the concavity 37 on the adaptive unit 36 is conveniently exposed to receive the cassette 38 (FIGS. 1 and 4). Side rails 44, 45 on the receiver 24 guide the adapter unit 36 into position in the receiver 24 while latch openings 47 in the bottom of the receiver 24 engage latches (not shown) provided conventionally in the receptacle 14. The latches enable detention of the receiver 24 but, when desired, allow release after the receiver 24 is fully inserted. However, release action will typically not be used. Posts 48 on the front of the receiver 24 are for attachment of the waste container bag 21 (FIG. 2).

The receiver 24 and the adapter 36 may be made wholly of metal, of plastic, or of different materials, inasmuch as these elements are not required to be sterile. The receiver 24 is kept in place for multiple surgical procedures while the adapter 36 is merely shifted in and out to enable replacement of the disposable sterile cassettes 38.

As best shown in FIGS. 1 and 4, the adapter unit 36 includes on its left side (as viewed from the front) a semicircular backup surface 50 opposite the roller pump 15 (FIG. 1) at the inserted edge. An open-topped tubing pathway 52 (FIG. 2) for an aspiration line extends across the backup surface 50 from the concavity 52 (FIG. 4) for the cassette 50, via a circular depression 54 for a flow dampener 56 (FIGS. 1 and 4). From the backup member 50 the aspiration line pathway 52 extends along one side (here the left) edge of the adapter unit 36 to the anterior edge, toward the waste container bag 21 on the front of the receiver 24. Thus an aspiration line 57 extending from the side of the cassette 38 can readily be threaded from the cassette 38 across the circular depression 54 for the flow dampener 56, past the backup surface 50 and out to the waste container bag 21. Opposite the VCS fitting 17 (FIG. 1), a protruding central cassette nose 58 (FIG. 4) also is proximate the VCS fitting 17, the nose 58 being bounded on opposite sides by the two sliders 31, 32 which span the distance to offset shoulders on the inserted cassette 38. The cassette 38, after insertion in the concavity 36, extends from the posterior end to the anterior end of the adapter unit 36.

The cassette 38, best seen in FIGS. 1, 2, and 4, comprises a shaped cassette body 60 having flat surfaces 62 (FIG. 4) along its sides for engaging the side walls of the adapter 36. Only the central protruding nose portion 58 of the cassette extends to the posterior end of the receiver 24 when the adapter 36 and cassette 38 are fully inserted.

Figure 3:
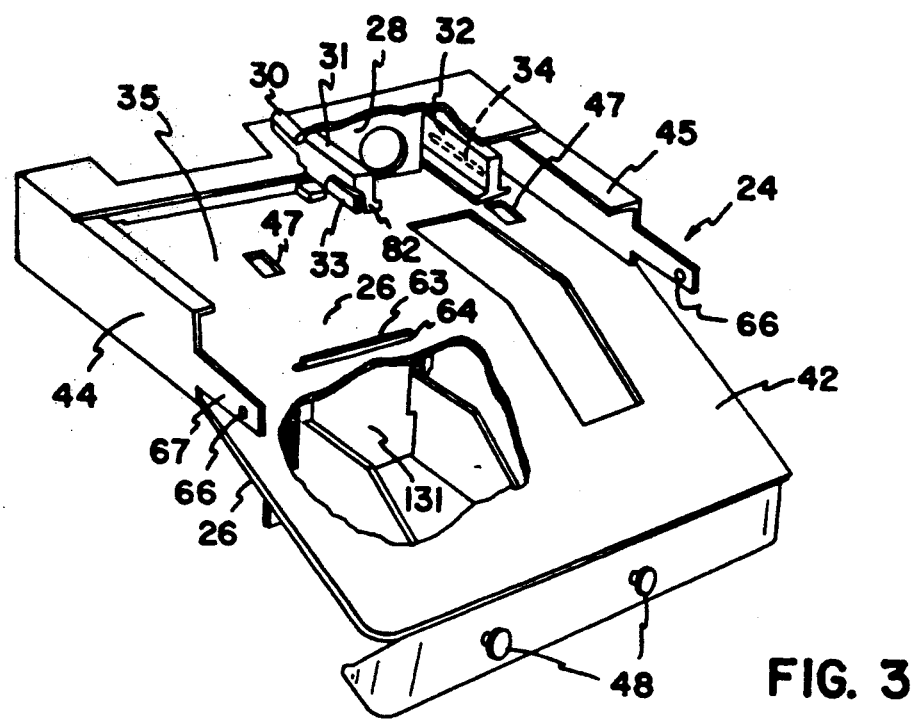
FIG. 3 is a perspective view, partially broken away, of one example of a receiver in accordance with the invention.
Figure 4:
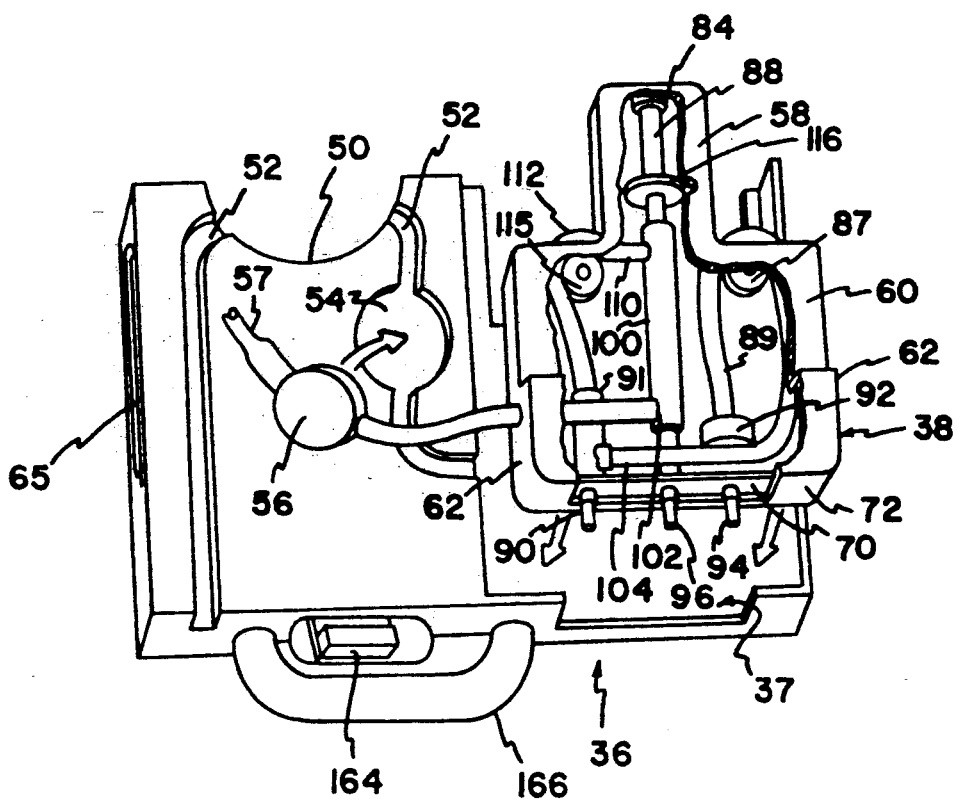
FIG. 4 is a perspective and partially exploded view, partially broken away, of an adapter and cassette in preloading positions.

To lock the adapter 36 in position, a spring loaded plate has an upper edge 63 extending through a slot 64 in the receiver body 26 at the upper end of the apron 42 (FIGS. 1 and 3). The plate edge 63 can be depressed to a limited extent so that the adapter 36 slides across it, then shifts into position against a transverse shoulder on the adapter 36. A slot 65 (FIGS. 1 and 4) extends along each side of the adapter 36 for engaging retaining prongs 66 on arms 67 extending from the side walls of the receiver 24. The adapter 36 is guided by the prongs 66 and can be pivoted when fully withdrawn from the receiver 54 onto the apron 42. The arrangement of the locking mechanism is more fully discussed hereafter in conjunction with FIGS. 5 and 6.

The cassette body 60 at its anterior edge includes a wall or bar 70 (FIG. 4) received in retainer elements 72 at each end, within which bar 70 are secured the ports and fittings for various tubing sections.

Each slider 31, 32 has a posterior end surface for engagement by the adjacent actuator 16 or 18 respectively and, at its opposite end, a protruding surface 82 (FIGS. 1 and 3) for clamping flexible tubing in the cassette 38. The interconnect portion of the disposable cassette 38 further includes a VCS grommet 84 (FIGS. 1 and 4), between the two sliders 31, 32 facing the vacuum control fitting 17, and an extension tubing 88 lying in the anterior direction from the VCS grommet 84.

Internally, as seen in FIG. 4, the substantially flat region of the cassette body 60 between the side surfaces 62 and the anterior face bar 70 includes a first backup surface 87 that is aligned with the irrigation slider 32. The first backup surface 87 is in the form of a circular post, about which an irrigation line 89 is wrapped. The irrigation flow path feeds into the cassette 38 at an irrigation input port 90 held in the bar 70 and couples to an irrigation manifold 91 having a shunt line to which the internal flexible irrigation tubing line 89 is coupled. The irrigation line 89 extends to the closest side edge of the cassette 38, passing about the backup surface 87 and through a one-way valve 92 that is retained in the holder bar 70 and then to an irrigation output port 94.

The aspiration line 22 from the handpiece (FIG. 2) is attached to an aspiration input port 96 (FIG. 4, also) coupled to an aspiration manifold 100 having a pair of junctions. A first of these junctions 102 couples to a first interior aspiration line 104 and then to the output aspiration line section 57 via the intervening flow dampener 56. A shunt junction 110 couples to a shunt line 112 that is positioned between the shunt slider 31 and a second backup surface 115, before being coupled to the irrigation manifold 91.

The aspiration manifold 100 also is coupled at its posterior end to a hydrophobic/bacterial filter 116 that leads into the anterior fitting 84 for the VCS connection in the console 12. In this example the hydrophobic/bacterial filter 116 is of circular outline and a slot opening 120 (FIGS. 1 and 2) is provided in the top wall of the cassette body 60 to permit a commercial filter to be used rather than requiring a specially modified shape of hydrophobic filter.

The tubing interconnect system of FIG. 4 is depicted as used with a specific system because of the number of control functions that are included in that system. These include the peristaltic pump, shunt control, vacuum control system, and irrigation flow control that make available to the surgeon particular operating modes through use of the handpiece and a foot control (not shown).

Figure 6:
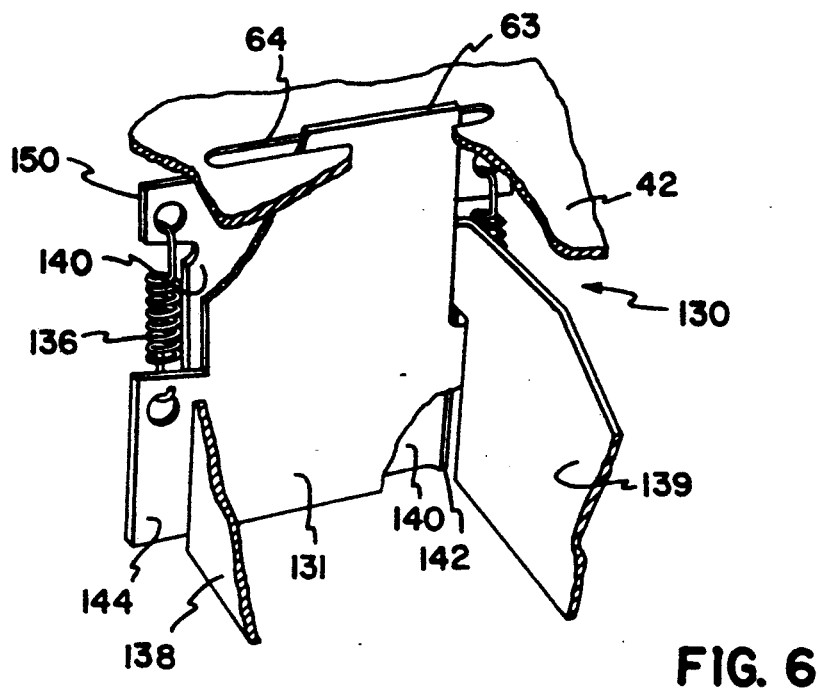
FIG. 6 is a fragmentary perspective view, partially broken away, of a spring-loaded locking mechanism for detachably holding an adapter and cassette on a receiver unit.
Figure 5:
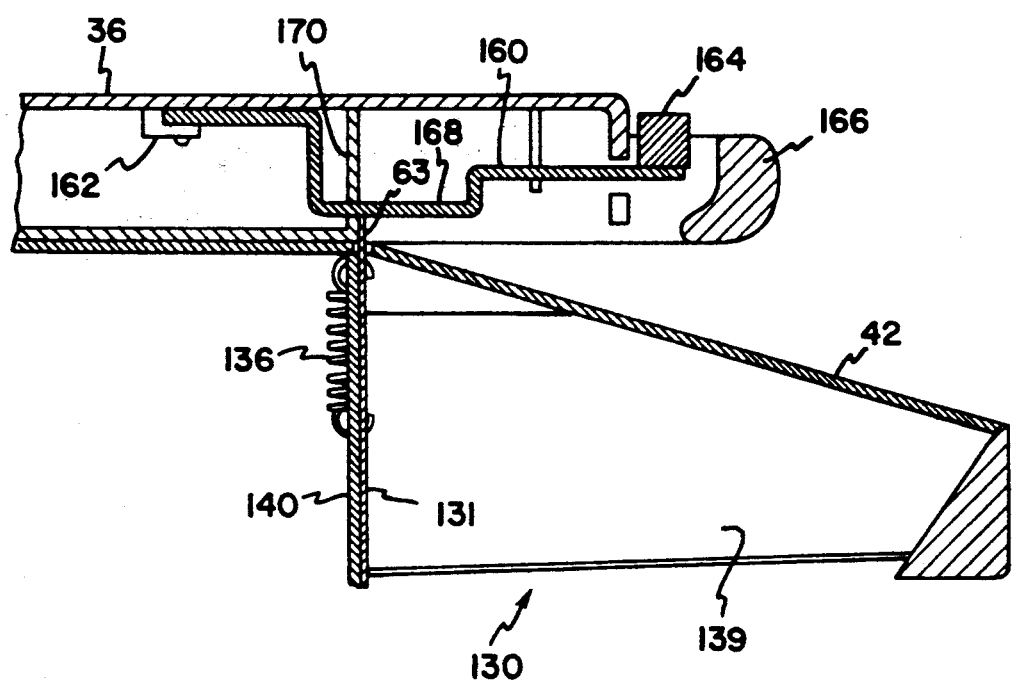
FIG. 5 is a side sectional view of the adapter unit seated in the loading position within the receiver unit of FIGS. 1 and 2.

The locking mechanism 130 for releasably holding the adapter unit 36 in position, referring now to FIGS. 3, 5 and 6, comprises an upstanding flat plate 131 having its upper edge 63 extending through the slot 64 in the receiver 24. The stop plate 131 is held in place under tension by side-mounted springs 136 and a U-shaped holding structure comprising a pair of side panels 138, 139 and a back plate 140 attached to the underside of the receiver apron 42. Vertical side slots 142 in the holding structure adjacent side wings 144 on the stop plate 131 receive the lower portion of the back plate 140, to guide the stop plate 131 up and down. The springs 136 interconnect the side wings 144 of the stop plate 131 with upper side tabs 150 on the back plate 140, thus biasing the stop plate 131 in the upward direction to hold the upper edge 132 above the slot 134. The upper limit of the side slots 142 determines how far the stop plate edge 132 protrudes above the slot 134.

The adapter unit 36, as best seen in FIG. 5, includes a latch lever 160 on its underside, in alignment with the protruding edge 163 of the stop plate 131. The latch lever 160 extends from a pivot base 162 interior to the adapter unit 36, outwardly in the anterior direction to an exposed release bar 164 within the limits of a handle 166 along the anterior edge of the adapter unit 36. A depending U-shaped segment 168 in the intermediate portion of the latch lever 160 spans and engages the upper edge 63 of the stop plate 131 when the adapter unit 36 is inserted in the receiver 24. In this position the stop plate edge 63 force the latch lever 160 up, and the side of the plate edge engages a shoulder 170 in the adapter unit 36, preventing withdrawal of the unit 36.

When the release bar 164 on the adapter unit 36 is pressed down, the latch lever 160 at the U-shaped segment 168 forces the stop plate 131 downward so that the upper edge 132 is flush with the upper surface of the receiver 24, clearing the exit path and allowing the adapter unit to slide away from the receiver 24 onto the front apron 42, for replacement or insertion of a cassette.

In operating the system, the receiver 24 is inserted into the receptacle 14 in the console 12 (FIGS. 1 and 2). The receiver 24 is guided directly into position by the side rails 44, 45, until the latch openings 47 in the bottom of the receiver 24 engage the system latches (not shown) incorporated in the console 12. The receiver 24 thereafter is left in position. It is assumed the adapter unit 36 is resting on the front apron 42 of the receiver 24 of the start of a typical insertion or replacement sequence. The used disposable cassette 38 may be removed and a new one inserted into the available concavity in the adapter unit 36. The attached aspiration line sections 104, 57 and intervening flow dampener 56 that extend from the side of the cassette 38 are set into the tubing pathway 52 in the upper surface on the left side of the adapter unit 36. Thus loaded, the adapter unit 36 may be slid into the receiver 24. This action interconnects the aspiration line 57 from the cassette 38 to the pump 15 and the vacuum control fitting 17 to the VCS grommet 84, while engaging the clamp actuators 16,18 against the sliders 31,32 (FIG. 1). With the receiver 24, adapter unit 36 and cassette 38 engaged in position, the end surface of the irrigation slider 32 directly opposes the irrigation line actuator 18, while the VCS grommet 84 faces and mates with the VCS line fitting 17. Concurrently, the shunt slider 31 engages the shunt line actuator 16 at its end surface 80 (FIG. 1), and the peristaltic pump 15 presses the aspiration tubing section 57 against the backup surface 50, pumping aspirated fluid when the pump 15 is rotated. The aspiration line 57 empties the aspirated fluid to the waste container bag 21. The first and second sliders 31, 32 in the receiver 24 respectively press the shunt tubing 112 against the second backup surface 115, and the irrigation line 88 against the backup post 87 respectively (FIG. 3). It can be seen that the combination thus far described reconfigures the system console 12, and forms a modified operating system with numerous advantages, as described below.

In the most often used mode of operation of the system, the shunt line 112 (FIG. 4) is held closed against the backup post 115 by the shunt slider 31 and the irrigation slider 32 is not shifted by the adjacent actuator 18 so that the irrigation tubing 88 is open. Thus sterile fluid flows from the source 19 through the irrigation manifold 80, the irrigation line 88, the one-way valve 92 and the irrigation output port 94 to the handpiece 13. Concurrently, the pump 15 is driven so as to create a negative pressure in the aspiration manifold 100 via the peristaltic pumping action on the tubing 57 at the backup surface 50. The negative pressure aspirates tissue and fluid from the handpiece back to the aspiration input port 98 through the manifold 94. The flow rate is varied with the foot control (not shown) in known fashion. The aspirated matter flows via the junction 102 through the aspiration line 104, the flow dampener 100, and out through the aspiration line 55 to the waste bag 21.

When suction is interrupted by matter occluding the handpiece, the back flush mode of operation is used. The irrigation slider 32 is engaged to clamp the irrigation tubing 88, stopping direct irrigation fluid flow to the handpiece. At the same time, the shunt slider 31 is released from the shunt line 112, opening the shunt line and providing sterile fluid from the input port 89 flow through the irrigation manifold 80, the line 112 and the aspiration manifold 100 back down to the handpiece 13. This momentary flow reversal is sufficient to dislodge any matter that may have accumulated in the orifices in the handpiece 13 and releases any in-line pressure.

When an operative procedure is completed, the disposable cassette 38 and associated tubing including the hydrophobic/bacterial filter 116, aspiration line 104, 57, and flow dampener 56 are removed and discarded. Then another disposable cassette 38 with sterile tubing is placed in position. The insertion, as seen in FIG. 4, is rapid and the geometry precludes incorrect insertion. The manual threading step is carried out without delay because the path invites correct placement. It is to be noted that the sliders 31, 32 are used repeatedly and that since they are only in contact with parts of a sterile cassette, there is virtually no danger of contamination even if a line should develop pinholes under repeated flexure. The receiver 24 and adapter unit 36 can be sterilized periodically and reused. Sterilization every day before commencing procedures would be a conservative approach yet would result in very significant savings. Because the tubing sections used in the back flushing mode are all in the disposable cassette 38 and because the clamps hold the tubing closed when power is off, the chances of contamination are minimized.

The lengths of tubing utilized within the disposable cassette, as described above, are short and follow substantially direct paths. Thus, the arrangement provided is compact and inexpensive and repeated use of the receiver enables significant cost reductions to be realized.

There are significant advantages in cost and convenience in this reconfigured system with no commensurate problems introduced because of the separate threading of the pump line. Indeed, because the cassette is so small and the geometry instinctively requires placement in the correct side of the adapter, and because loading/unloading steps are carried out on the apron of the receiver, placing the aspiration line into position in the pathway provided is very straightforward and rapid. The economic benefits of this approach are substantial because disposable costs are reduced to a minimum.

What is claimed is:

1. A system for use in a cassette receiving surface of a console having a flow control mechanism for controlling the flow of sterile fluid to an operative site from a source and pump means for controlling the flow of non-sterile fluid from the operative site to a waste collection means, comprising:
    a receiver configured to seat against the cassette receiving surface and including means for holding a cassette adapter defining an interior volume open to the side opposite the console and a slider disposed to engage a flow control mechanism extending from the console;
    a cassette adapter in the form of a panel slidably fixed to the receiver and having a cassette receiving volume open to the side opposite the console, the adapter being aligned with the slider and having an adjacent open-tapped tubing pathway including backup surface means in alignment with the pump means of the console; and
    a disposable cassette configured to mate within the interior volume in the cassette adapter, the cassette including external fitting means for coupling sterile fluid flows into and out of the cassette, and an external tubing section positioned to be insertable into the tubing pathway when the cassette is inserted within the adapter.

2. A system as set forth in claim 1 above, wherein the receiver forms a service apron for supporting the cassette adapter while the disposable cassette is inserted into the cassette adapter.

3. A system as set forth in claim 1 above, wherein the console includes a peristaltic pump means for drawing fluid from the operative site in response to the flow control mechanism, and where the receiver includes reciprocable means for blocking fluid flow in response to system actuation of the flow control mechanism.

4. A system as set forth in claim 3 above, wherein the cassette adapter includes at least one backup surface disposed opposite the reciprocable means.

5. A system as set forth in claim 4 above, wherein the disposable cassette includes flexible tubing for sterile fluid interposed between the reciprocable means and the backup surface to be clamped selectively in response to operation of the flow control mechanism against the reciprocable means.

6. A system as set forth in claim 1 above, wherein the flow control system includes a peristaltic pump and the cassette adapter includes means for directing the non-sterile flows from the operative site past the pump to the waste collection means.

7. A system as set forth in claim 1 above, wherein the flow control system includes a pump and the receiver includes reciprocal means for blocking fluid flow in response to system actuation of the flow control mechanism, the cassette adapter includes means for directing non-sterile fluid from the operative site to the waste collection means and the disposable cassette includes means for transferring sterile fluid from the source to the operative site under control of the flow control mechanism.

8. An apparatus for use with an aspiration/irrigation system having a cassette-receiving receptacle including a roller pump disposed to engage an adjacent flexible line, a control means for a vacuum control orifice and at least one actuator for compressing flexible lines, the apparatus comprising:
    a receiver insertable within the receptacle, the receiver including an interior volume accessible to the exterior of the console when the receiver is inserted, and at least one slider disposed to engage an actuator;
    a cassette adapter in the form of a panel slidably insertable in the receiver and having a cassette receiving volume open to the side opposite the console and a first backup surface facing the pump roller; and
    a disposable cassette mechanism having an aspiration input fitting, an irrigation input fitting and an irrigation output fitting, the cassette being insertable in the cassette adapter and including a second backup surface, flexible tubing and an interior line, said backup surface being disposed opposite the interior end of the first slider when the cassette is inserted in the cassette adapter, said tubing being coupled between the irrigation input and irrigation output and interposed between the interior end of the slider and the second backup surface, said interior line intercoupling the aspiration input line to the aspiration line fitting of the receptacle.

9. The invention as set forth in claim 8 above, wherein the receiver includes a second slider, the cassette mechanism includes a third backup surface and a shunt line coupling the irrigation input to the aspiration input, the shunt line also incorporating a flexible line interposed between the second slider and the third backup member in the cassette mechanism.

10. The invention as set forth in claim 9 above, wherein the cassette mechanism incorporates an irrigation manifold coupled to the irrigation input fitting, and an aspiration manifold coupled to the aspiration input fitting, and wherein the shunt line intercouples the irrigation manifold to the aspiration manifold.

11. The invention as set forth in claim 10, wherein the aspiration input line includes a flow dampening means therein and is further coupled to a vacuum control connection.

12. The invention as set forth in claim 11 above, wherein the cassette has an anterior position thereof when inserted and includes means for suspending a waste bag therefrom at the anterior portion.

13. The invention as set forth in claim 12 above, wherein the receiver comprises a pair of side rails disposed to engage side edges of the receptacle when the receiver is inserted.

14. The invention as set forth in claim 13 above, wherein the receiver further comprises means for engaging the receptacle, and wherein said cassette adapter includes means for slidably engaging the side rails of the receiver.

15. The invention as set forth in claim 14 above, wherein the first backup surface comprises a substantially semicircular boss and wherein the cassette includes, in the aspiration line, a female aspiration fitting engaging the male aspiration fitting in the receptacle, and wherein the aspiration line manifold includes a hydrophobic bacteriological filter and an extension tube engaging the female aspiration fitting.

16. The invention as set forth in claim 15 above, wherein the system includes a pump roller, first and second clamp actuators and a suction control means for drawing fluid from an operative site disposed along an interior surface in the receptacle, first and second slider ends extending from the inserted edge of the receiver into the region of the cassette for engagement against the respective flexible lines when the clamp actuators are energized, and wherein the cassette adapter includes a leading edge having the first backup surface.

17. The method of using sterile disposable tubing sets in conjunction with a system having a receptacle for receiving disposable cassettes, the receptacle including tubing engaging a pump, a variable position occluder accessible to a vacuum control system orifice and at least one actuator for clamping a line in an inserted cassette, comprising the steps of:

inserting a receiver unit having a cassette adapter slidably fixed thereto for providing a cassette receiving volume open to the side opposite the console and an open-tapped pathway including a peristaltic pump backup surface in alignment with peristaltic pump receiver;

sliding the cassette adapter away from the receptacle onto an apron extending from the receiver;

inserting a disposable cassette into the cassette adapter by first placing an aspiration line attached to the disposable cassette into a channel disposed within the cassette adapter;

lowering the posterior end of the cassette into the cassette adapter;

lowering the anterior end of the cassette into the cassette adapter while aligning a guide slot attached to the side of the cassette into a guide notch disposed in the corresponding side of the cassette adapter;

sliding the loaded cassette adapter into the receiver thus interconnecting the cassette to the pump line, the vacuum control orifice and the clamp actuator; and interconnecting inlet and outlet lines to the cassette.

18. A combination for installation in a console having a receptacle in which a peristaltic pump and at least one actuator are aligned but spaced apart on different sides within the receptacle, comprising:

a receiver having an open interior volume configured to mate within the receptacle, the receiver having an extending front apron for operator use in cassette replacement when the receiver is inserted in the receptacle, the receiver providing unobstructed access to the pump;

an adapter unit insertable in the open interior volume and having a pump side and an actuator side, the pump side including means for placement of tubing in operative relation to the pump and the actuator side including means for receiving a cassette with interior tubing;

a cassette with interior tubing configured to fit in the means for receiving in the adapter unit; and means coupling at least one actuator to the tubing in the cassette when inserted in the receiver.

19. A combination as set forth in claim 18 above, wherein upper portions of the adapter unit and cassette are configured to be accessible on the front apron while the receiver is within the receptacle, and the cassette includes tubing placeable in the means of the adapter unit for coaction with the pump when the adapter unit and cassette are inserted.

20. A combination as set forth in claim 19 above, wherein the receiver includes at least one slider in alignment with the at least one actuator and cooperative with tubing in the cassette.

21. A combination as set forth in claim 18 above, further including means coupled to the receiver for releasably retaining the adapter unit in the inserted position.

22. A combination as set forth in claim 21 above, wherein said means for releasably retaining the adapter unit comprises a spring loaded step means protruding into the open interior volume of the receiver adjacent the apron, and wherein the adapter unit includes a latch lever means actuable by an operator to depress the protruding stop means and allow release of the adapter unit.

23. A combination as set forth in claim 22 above, wherein the receiver includes means defining a slot in the path of the adapter means the spring loaded stop means comprises a stop plate principally disproved below the receiver and including an upper edge protruding through the slot in the receiver, and spring means for biasing the stop plate upwardly, and wherein the latch lever means comprises an elongated member coupled to the underside of the adapter unit in the interior thereof and extending to the front side of the adapter unit, the elongated member including a segment engaging the upper edge of the stop plate, and wherein the adapter unit includes a underside shoulder positioned for engagement against the protruding edge of the stop plate.

24. A cassette mechanism for use in an irrigation/aspiration system wherein irrigation input and output tubing lines and shunt tubing lines are to be internally changed, comprising:
- a cassette housing having a substantially rectangular principal body forming three sides thereof and a central nose portion protruding from side shoulders on the fourth side thereof, the side shoulders including apertures for access to tubing therein;
- internal tubing including irrigation tubing and shunt tubing having portions adjacent the respective apertures;
- external ports for irrigation input and output and for aspiration input disposed on one side of the cassette body; and
- an aspiration output line extending from a second side of the cassette body.

25. A cassette mechanism as set forth in claim 24 above, wherein the rectangular body includes internal backup surfaces facing the apertures in the side shoulders, wherein the aspiration output line includes flow dampener means, and wherein the nose portion of the cassette includes vacuum control system fitting means.

* * * * *